US010821025B1

(12) United States Patent
Stravitz

(10) Patent No.: US 10,821,025 B1
(45) Date of Patent: Nov. 3, 2020

(54) EYE GUARD/SHIELD WITH GUIDE CHANNELS

(71) Applicant: Dooli Products, LLC, New York, NY (US)

(72) Inventor: David M. Stravitz, New York, NY (US)

(73) Assignee: Dooli Products, LLC, New York, NY (US)

( * ) Notice: Subject to any disclaimer, the term of this patent is extended or adjusted under 35 U.S.C. 154(b) by 0 days.

(21) Appl. No.: 16/818,582

(22) Filed: Mar. 13, 2020

Related U.S. Application Data

(60) Provisional application No. 62/935,755, filed on Nov. 15, 2019, provisional application No. 62/884,033, filed on Aug. 7, 2019.

(51) Int. Cl.
*A61F 9/04* (2006.01)

(52) U.S. Cl.
CPC .................................. *A61F 9/04* (2013.01)

(58) Field of Classification Search
CPC ..................... A61F 9/04; A61F 13/124; A61F 2013/00497; A61F 2013/00502; A61F 9/007; A61F 13/0243; A61F 13/025
USPC ................................ 128/858; 602/47, 52, 74
See application file for complete search history.

(56) References Cited

U.S. PATENT DOCUMENTS

| | | | | |
|---|---|---|---|---|
| 3,300,786 A | * | 1/1967 | Rosenvold | A61F 13/124 2/15 |
| 4,117,842 A | * | 10/1978 | Hutchins | A61D 7/00 424/448 |
| 4,682,371 A | * | 7/1987 | Heltman | A61F 13/124 128/858 |
| 4,709,695 A | * | 12/1987 | Kohn | A61F 9/04 128/858 |
| 4,862,902 A | * | 9/1989 | Goffman | A61F 9/04 128/858 |
| 4,969,472 A | * | 11/1990 | Langley | A61F 9/04 128/858 |
| 5,004,333 A | * | 4/1991 | Bruhl, Jr. | A61F 9/00 128/858 |
| 2011/0034849 A1 | * | 2/2011 | Cooks | A61F 13/124 602/74 |

\* cited by examiner

*Primary Examiner* — Kari K Rodriquez
(74) *Attorney, Agent, or Firm* — Brian Roffe

(57) ABSTRACT

Eye shield including a curved body having a size to cover a person's eye. The body has a concave side configured to face the eye and an opposite convex side. The body has a circumferential edge and openings in a central region. The body includes a spaced apart pair of notches each extending inward from the circumferential edge but not communicating with the openings. Each notch defines an opening between opposed surfaces. A piece of adhesive tape wider than a distance between the notches passes through both notches alongside the concave side of the body between the notches and over the convex side of the body laterally outside of the notches. Another body has a central region made of an optically clear material and a peripheral region surrounding the central region made from a resilient flexible material and which defines the circumferential edge of the body.

20 Claims, 20 Drawing Sheets

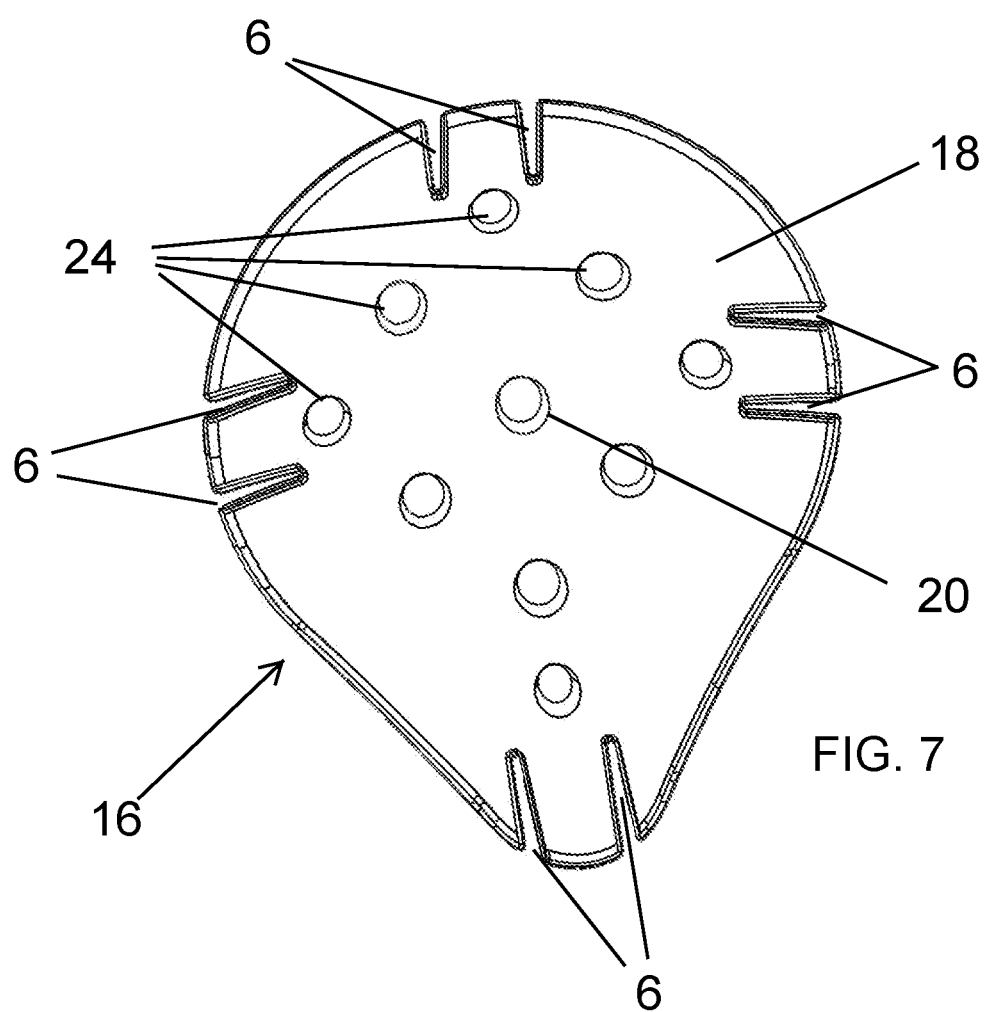

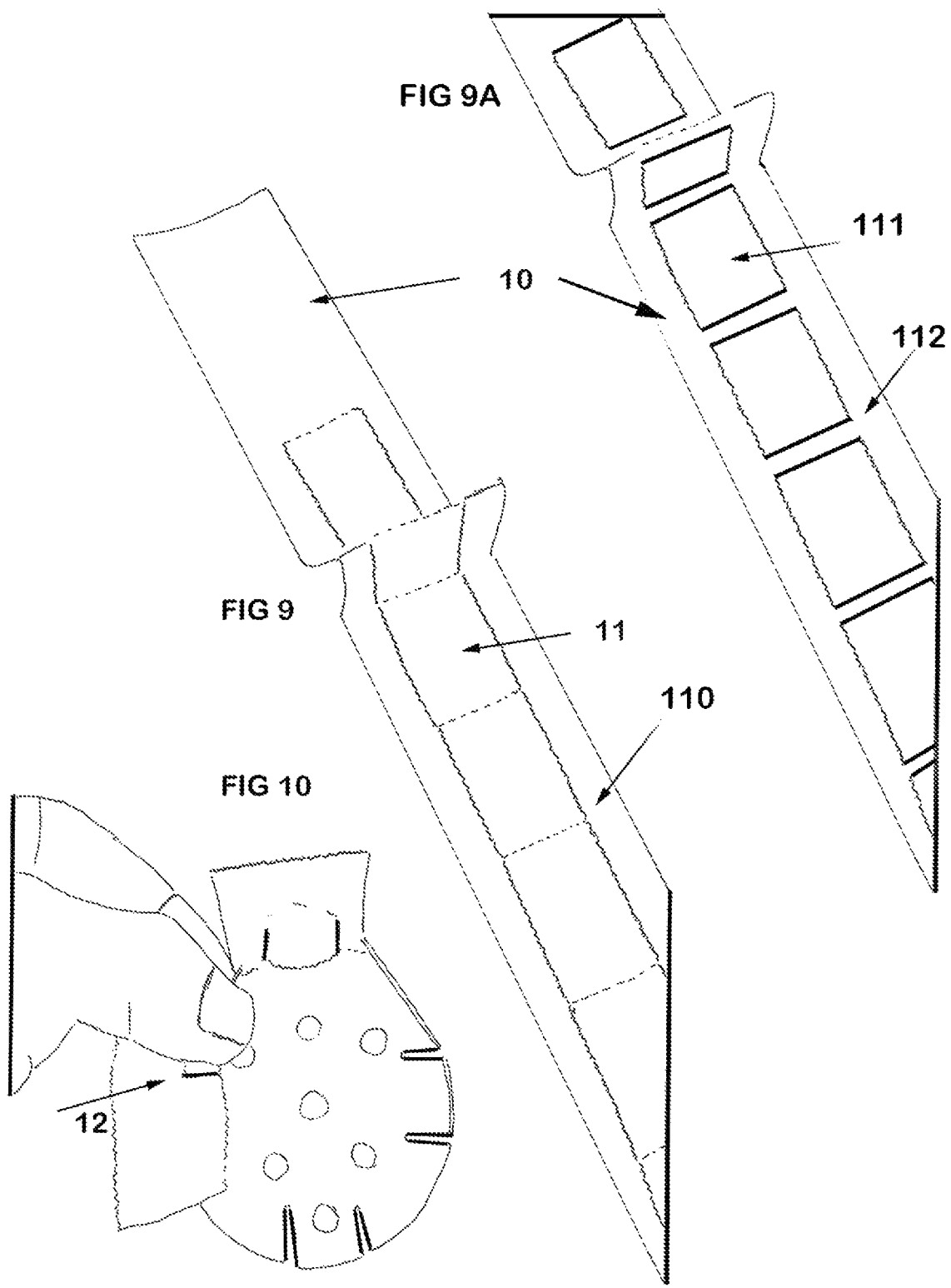

EYE GUARD/SHIELD WITH GUIDE CHANNELS

FIELD OF THE INVENTION

The present invention relates generally to an improved post-surgery and general eye protective guard (shield) with guided channels for a sanitary bandage strip that engages the eye shield. The present invention also provides pre-sized strips for use with the eye shield that do not impede or block vision.

BACKGROUND OF THE INVENTION

Cataract surgery is the most common procedure performed by the ophthalmic surgeon. This year, 3.6 million cataract procedures will be performed in the United States and more than 20 million will be performed worldwide, according to some estimates.

Eye shields are commonly used for up to a week following eye surgery such as cataracts. An eye shield is usually used at night only, and is typically clear. Patients typically have the following items ready in front of a mirror: one, two or more pieces of sanitary adhesive tape 6 to 8 inches long. This tape is typically provided by the hospital or can be purchased from a pharmacy.

For use, the patient places the eye shield over the operated-upon eye with a curved side of the eye shield typically against their nose. They put the eye shield in place with the tape across the top of the eye shield, as well as the bottom region of the eye shield. An upper strip of tape should go from the middle of the forehead to the middle of the ear. A lower strip of tape is used to secure the bottom region of the eye shield. The patient is instructed to wash the eye shield and glasses with soap and water regularly.

While this procedure has been successful in the majority of cases, one is prone to adhere the tape strips of different length each night during use. Longer tape strips may from time to time tend to irritate the skin. This is often caused by the eye shield being not so carefully removed. Many patients have reported breaking the skin and causing bleeding. Other patients find that one or more of the tape strips block their vision and find themselves often re-positioning the strips so as not to not interfere with vision. This may frustrate the patient who may be ultra-sensitive to post-operative changes. A misaligned strip of tape could exacerbate the condition.

The majority of these eye shields are high quality injection molded plastic, water clear and typically unbreakable. This assists the process of healing and offers comfort and protection.

Some are superior unbreakable polycarbonate (LEXAN™) and reasonably water clear and distortion free. Others are also water clear, but of lesser quality breakable acrylic (PLEXIGLAS™). Quality is in the injection mold construction. The cavity surface must be plano flat and reasonably distortion-free therefore. Furthermore, the injection molds to produce the eye shields need to be diamond polished to a mirror finish.

Some eye shields are for the left eye, some are for the right eye and many are universal to both eyes. All have through-holes for ventilation. These holes vary in location from one manufacturer to another. A significant number, if not all, have a non-interrupted continuous perimeter outside edge.

There are numerous manufacturers, suppliers and distributors of clear protective post-surgery eye shields. It is believed that they all have one thing in common, a non-interrupted continuous perimeter outside edge to enable one or more strips of tape to go over (adhere) to the top shield surface and randomly engage the patient's skin. For years, this has been the industry standard with no required advancements other than rearranging the vent holes and slight configuration changes from one supplier to another.

OBJECTS AND SUMMARY OF THE INVENTION

It is an object of at least one embodiment of the present invention to provide an improved eye shield or guard typically used in post-operative eye surgery such as cataracts, etc.

It is an object of at least one embodiment of the present invention to provide an eye shield or eye guard including defined parallel interrupted channels along the perimeter that provide limits for pre-sized sanitary adhesive tape to securely engage the shield or guard in at least two places.

It is another object of at least one embodiment of the present invention to provide an eye shield or eye guard that can be applied to a person over their eye using a continuous roll of adhesive that is cut to torn to a desired size.

It is an object of at least one embodiment of the present invention to provide an eye shield or eye guard that ensures that vision of the user is not impeded by randomly placed tape as in the case of conventional eye guards. Thus, even if two or more strips of different (random) sizes of adhesive tape are used with the eye shield or eye guard, as long as they are in channels of the eye shield or eye guard, they do not impede vision when installed on the person.

It is an object of at least one embodiment of the present invention to provide an eye shield or eye guard with a plurality of substantial parallel channels.

It is an object of at least one embodiment of the present invention to provide an eye shield or eye guard that preferably is associated with strips or rolls of pre-sized die-cut adhesive strips that are wider than the channels. Use of pre-sized adhesive strips is preferable, but not imperative.

In order to achieve one or more of these objects, an improvement to the myriad of substantially the same eye shields currently on the market would be to provide interrupted channels, notches or interruptions in the eye shield that enable substantially identical sized die-cut strips to engage the channels. This guarantees no visual blockage and easy adherence to both the inside and outside of the eye shield and minimal engagement to the patient's skin. These channels may be tapered so as to facilitate rapid engagement to the invention and then the patient. These channels are configured such that there are at least two channels per set and the eye shield in accordance with the invention requires preferably one or more sets.

Another embodiment of an eye shield in accordance with the invention includes a curved, preferably overmolded body having a size to cover an eye of a wearer, the body having a concave side configured to face the eye of the wearer, an opposite convex side, a circumferential edge and openings in a central region. The body has a central region made of an optically clear material and a peripheral region surrounding the central region made from a resilient flexible material and which defines a circumferential edge of the body. The central region may be made from acrylic or polycarbonate or other optically clear material. The peripheral region is preferably made of elastomeric material.

An attachment structure attaches the central region to the peripheral region, e.g., cooperating tongue or groove formations. The peripheral region includes resilient, flexible edges, and may be made of material having a hardness of from about sponge-like Shore 30A to about Shore 65A durometer. The other features of the first embodiment may be applied in this embodiment as well.

For example, the overmolded body may include two or more spaced apart pairs of notches each extending inward from the circumferential edge but not communicating with the openings, each notch defining an opening between opposed surfaces. A piece of adhesive tape may be provided wider than a distance between each pair of notches and that passes through both notches in the pair of notches with the piece of adhesive tape being alongside the concave side of the body between the pair of notches and over the convex side of the body laterally outside of the pair of notches, or vice versa. The notches may each include a pair of parallel edges to form a parallel opening. Alternatively, the notches may each include a pair of edges that taper toward one another to form a tapered opening.

In another embodiment, the body includes four spaced apart pairs of notches each extending inward from the circumferential edge but not communicating with the openings, each notch of each of the four pairs of notches defining an opening between opposed surfaces. In this case, the eye shield includes an additional piece of adhesive tape that passes through both notches in a respective pair of notches with the piece of adhesive tape being alongside the concave side of the body between the respective pair of notches and over the convex side of the body laterally outside of the additional pair of notches, or vice versa.

In some embodiments, the body has four sides and includes three additional spaced apart pairs of notches each extending inward from the circumferential edge but not communicating with the openings. Each notch of each three additional pair of notches defines an opening between opposed surfaces, the pairs of notches each being arranged on a respective side of the body such that each side of the body includes a single pair of notches.

The invention also relates to a system attachable to a person's face to cover an eye of the person. This system includes an eye shield as in any of the embodiments described above and a strip including pieces of adhesive tape at least equal in number to the number of pairs of notches. Each piece of adhesive tape has a length larger than a distance between a respective pair of notches. The eye shield is attached to the face of person to cover the person's eye by passing each piece of adhesive tape through both notches of the respective pair of notches. The pieces of adhesive tape may be separated on the strip by perforated score lines or by separation areas.

A method for covering an eye of a person in accordance with the invention includes the step of positioning the eye shield against the face of the person over the eye such that the concave side faces the person's face. The method then entails passing a respective piece of adhesive tape having a length larger than a distance between each of the notches of a respective pair of the notches through both of the notches of the respective pair of notches and against the face of the person to adhere the eye shield to the person's face. This may entail passing the respective piece of adhesive tape alongside the concave side of the body between the notches of the respective pair of notches and over the convex side of the body laterally outside of an area between the notches of the respective pair of notches. Each piece of adhesive tape may be removed from a strip including pieces of adhesive tape at least equal in number to the number of pairs of notches.

Preferably, the strip includes sufficient adhesive tape pieces to cover the expected duration of use of the eye shield, for example, to cover a desired one week of nightly applications. For example, twenty-eight pre-sized strips would cover use of four fresh strips nightly for seven days, or fourteen pre-sized strips would cover two fresh strips nightly for seven days.

BRIEF DESCRIPTION OF THE DRAWINGS

The invention, together with further objects and advantages thereof, may best be understood by reference to the following description taken in conjunction with the accompanying drawings, wherein like reference numerals identify like elements, and wherein:

FIG. 7 is a frontal view of the eye shield in accordance with the invention with the channel opening being tapered;

FIG. 9 is a partial view of a strip of die-cut peel-off adhesive tape separated individually with perforations and adhered to a strip of paper for easy removal;

FIG. 9A is a partial view of a strip of die-cut peel-off adhesive tape separated individually with spaces adhered to a continuous strip of paper for easy removal;

FIG. 10 is frontal view of the eye shield in accordance with the invention facing the direction toward the patient's eye (concave) with one die-cut strip secured to two channels, and one die-cut strip engaged in the first channel and ready to engage the second channel;

DETAILED DESCRIPTION OF THE DRAWINGS

Referring to the accompanying drawings, FIGS. 1-4 are views illustrating examples of conventional placement of prior art right eye shield (FIGS. 1 and 2) and left eye shields (FIGS. 3 and 4) that are secured by adhesive tape to a post-operative patient as a means to protect the operative eye. This securing is typically done at night, although it may be done during the day as well, to keep the eye safe from engaging surfaces that may cause harm. Normally this may last for a full week. Often, and unfortunately, the tape interferes with vision (see FIGS. 2 and 4), and each time new tape is adhered to the body of the eye shield, lengths and placement (contact) will be different from one application to the other. In fact, in a week's time, the patient will have likely placed 14 different size strips of adhesive tape in likely 14 different locations. This combination/permutation of placement and size of tape strips is in the hundreds or much more, especially if the patient does this without any assistance convalescing at home. Most likely, vision in the affected eye will be in one fashion or another blocked or at least partially blocked during use of the eye shield. This does not take in the possibility of trial and error which further affects application time, and other factors.

Figure 1:
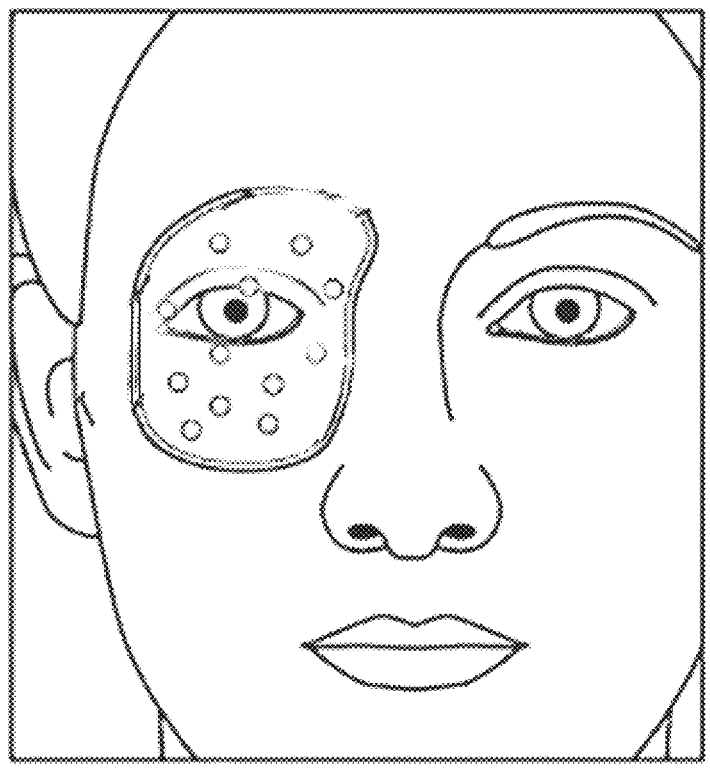
FIG. 1 is a frontal view of the proper positioning of a conventional clear protective right eye shield.
Figure 2:
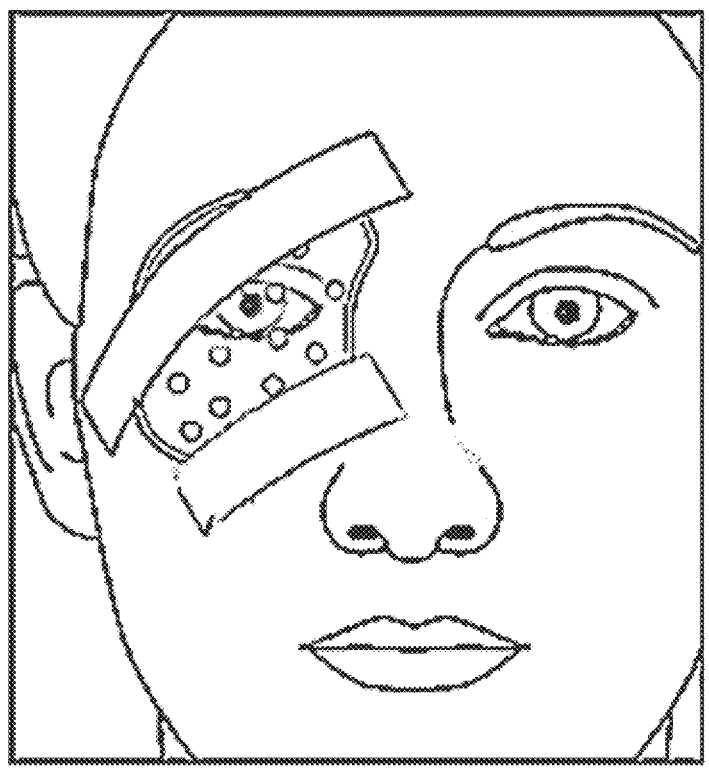
FIG. 2 is a frontal view of the proper positioning of the conventional clear protective right eye shield with two strips of adhesive tape securing the eye shield to the top surface of the eye shield and the patient.
Figure 3:
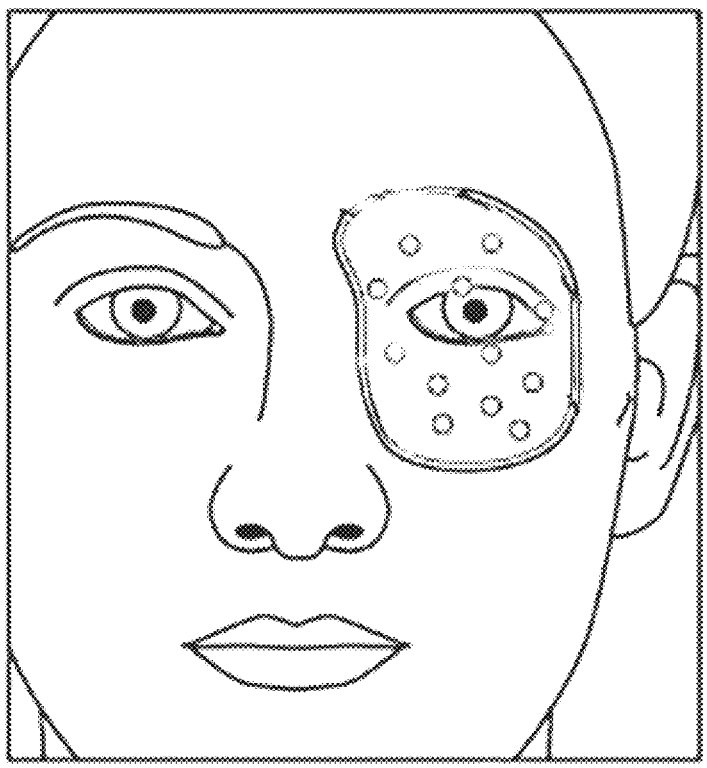
FIG. 3 is a frontal view of the proper positioning of a conventional clear protective left eye shield.
Figure 4:
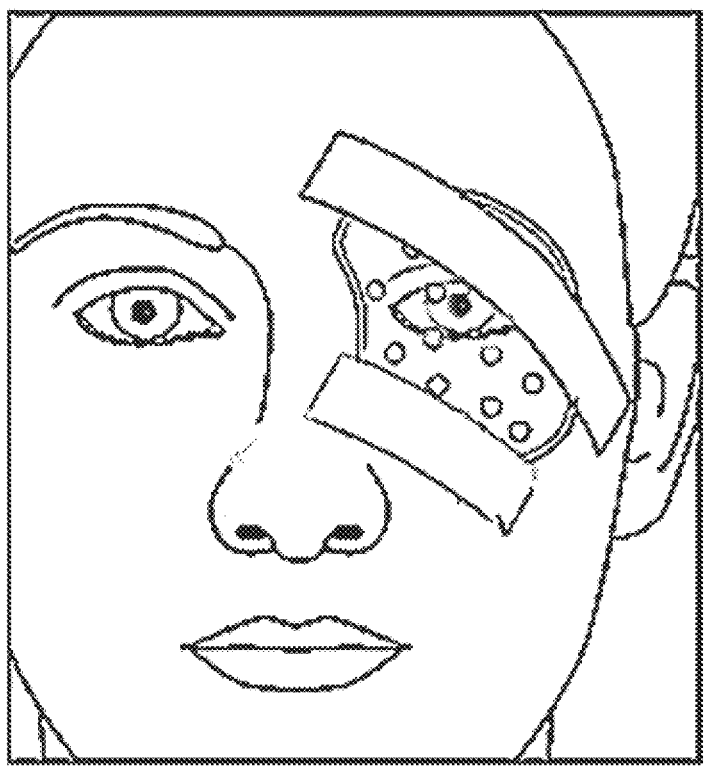
FIG. 4 is a frontal view of the proper positioning of the clear protective left eye shield with two strips of adhesive tape securing the eye shield to the top surface of the eye shield and the patient.
Figure 5:
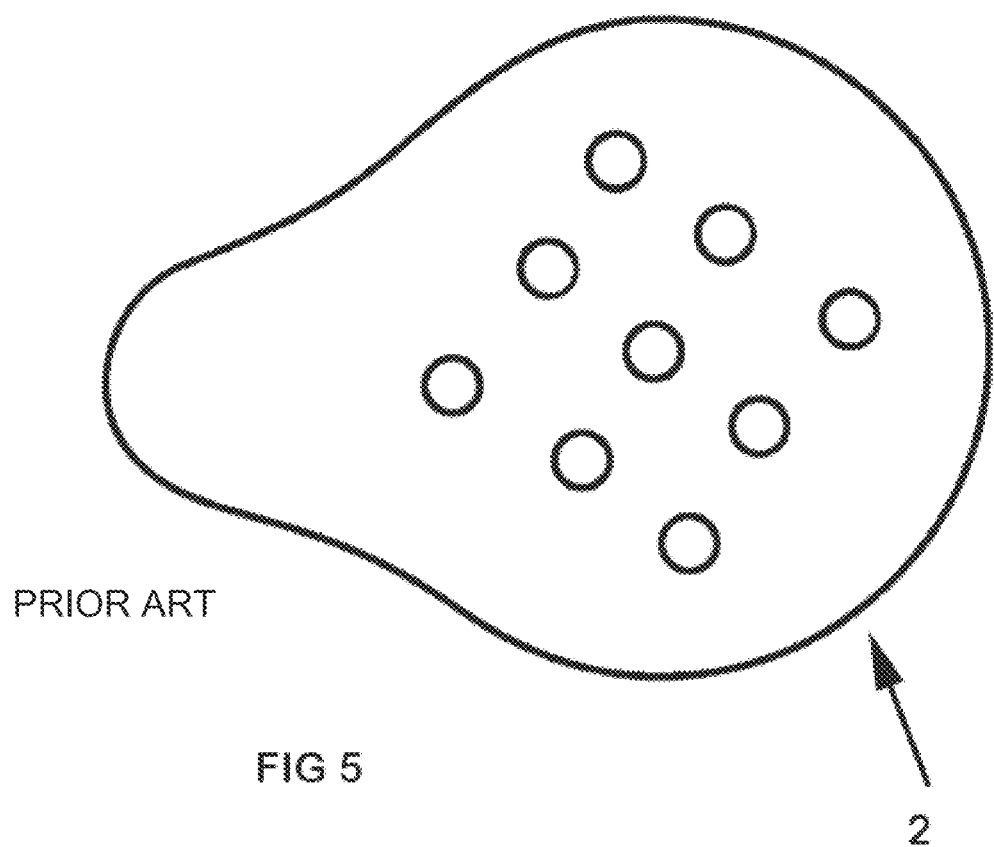
FIG. 5 is a frontal view of a conventional clear eye shield.

FIG. 5 is a view of a conventional eye guard of universal design which can be affixed to both the left and right eyes. The perimeter 2 is continuous (with no interruptions) and is designed to enable it to be affixed to the affected eye by taping the body in one or more places over the convex side (outside) of the body and then to the patient's skin. The concave (inside) side of the body faces the eye.

Figure 6:
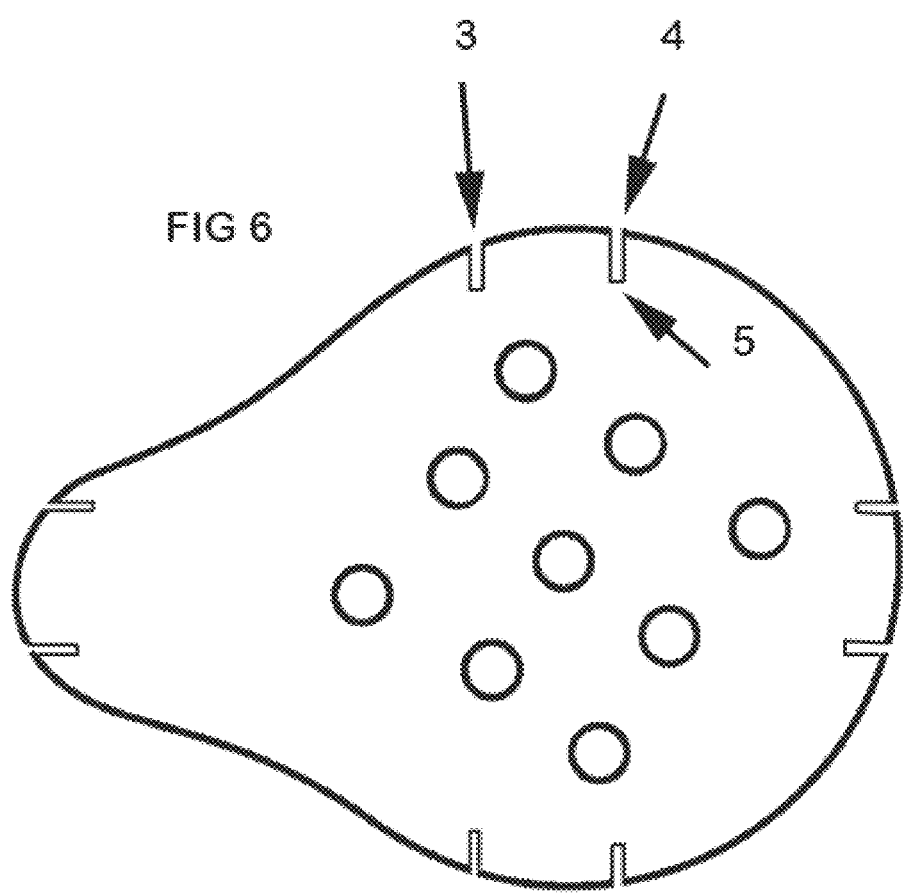
FIG. 6 is a frontal view of the eye shield in accordance with the invention clear eye shield showing interrupted channels with the opposite ends of the channels being substantially parallel.

FIG. 6 is a view of the improved invention which, while the body is similar in shape, is unlike the conventional eye guard (shown in FIG. 5), in that it has two or more (a plurality) of interruptions or notches along the perimeter or circumferential surface or edge of the body. These interruptions or notches typically include, comprise or consist of two open channels 3, 4 that extend inward to a center of the eye shield from the perimeter or circumferential surface. The channels 3, 4 allow the passageway of adhesive tape to spool through and rest at the bottom of the open channel(s) 3, 4. As used herein, adhesive tape is considered to be any type of adhesive element, component or member that includes a substrate and adhesive material on at least one side of the substrate. It is synonymous with an adhesive strip, an adhesive roll, an adhesive piece and other terms in the art to which this invention pertains.

Channels 3, 4 may be parallel openings 5 as shown in FIG. 6 or tapered openings 6 as in the body 18 of the eye shield 16 shown in FIG. 7. Parallel openings means that the openings are defined by two straight (or substantially straight) lines or internal edges with a space therebetween. The internal edges may be contiguous with the peripheral or circumferential surface or edge of the body.

It is possible to have channels all the way around the perimeter of the eye shield and as such, the person installing the eye shield can decide where to place the strips of adhesive tape. For example, one could place the tape in opposed pairs of channels, i.e., engaged with notches on opposite sides of the eye shield. The opposed pairs of channels may be parallel to one another, or enable placement of parallel pieces of adhesive tapes, although this is not required.

Figure 7A:
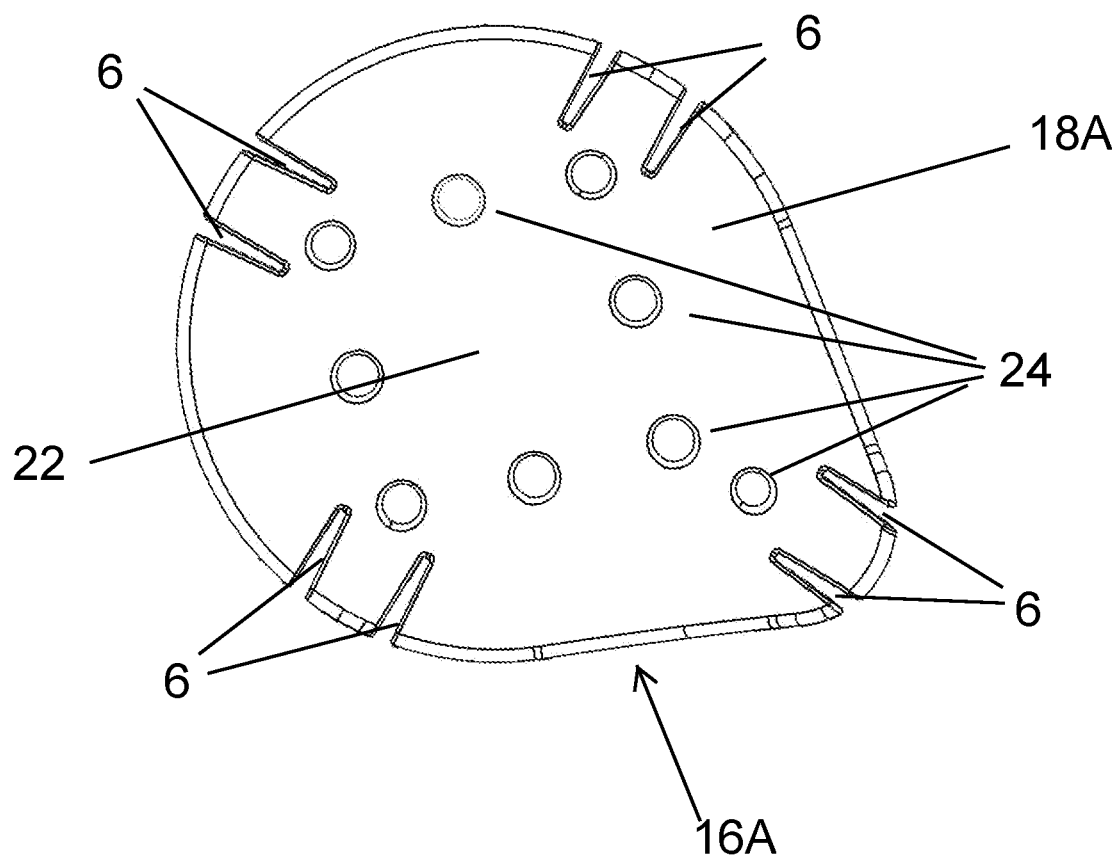
FIG. 7A is a frontal view of another embodiment of an eye shield in accordance with the invention with the channel opening being tapered similar to the embodiment shown in FIG. 7.

FIG. 7A shows a variant of the eye shield 16 shown in FIG. 7 and which is designated 16A wherein the body 18A of the eye shield 16A has a central region 22 that is lacking the central opening 20 shown in the body 18 of the eye shield 16 in FIG. 7. The presence, number and position of the openings 24 in the body 16, 16A, including the optional presence of the central opening 20, is a matter of discretion to the fabricator of the eye shield 16, 16A in accordance with the invention.

Figure 7B:
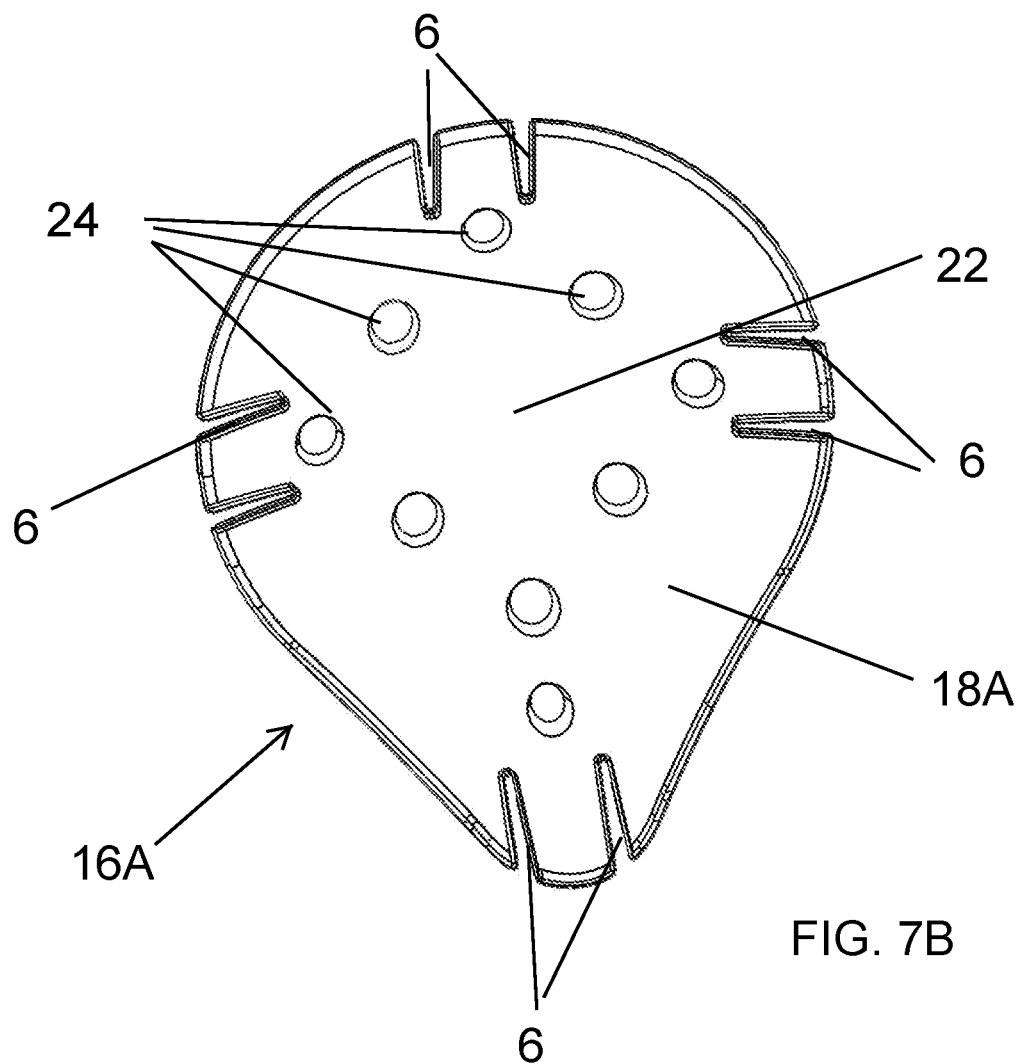
FIG. 7B is a perspective view of the eye shield shown in FIG. 7A.

FIG. 7B is a perspective view of the eye shield 16A shown in FIG. 7A wherein it is possible to view the thickness or depth of the body 18A of the eye shield 16A through the openings 24. The thickness of the body 18A in one embodiment is about 0.0625 inches (1/16") and each opening 24 should taper to enable release the body 18A when injection molded. Injection molding is considered to be a preferred method, but not an exclusive method, to fabricate the body 18A of the eye shield 16A, as well as the body of other eye shields disclosed herein. Thus, from FIG. 7B, it is possible to view through the openings 24 and see the realistic inner taper thereof so that the body 18A can be released from the injection molding machine because it has an appropriate taper (draft).

There are four sets of open channels 3, 4, two in each set forming pairs of open channels 3, 4, with each set of channels being on a respective side of the eye shield. The notches do not communicate with the openings in the body of the eye shield which are generally in a central region of the body.

Figure 8:
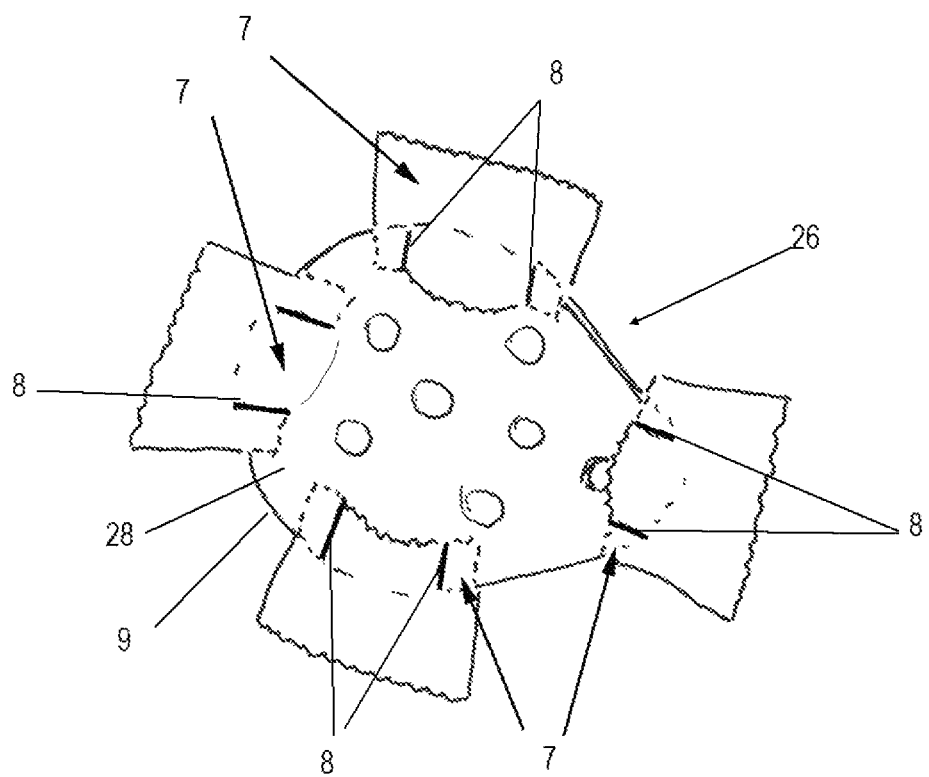
FIG. 8 is a frontal view from the concave side (side facing the patient's eyes) with four die-cut adhesive strips engaging four sets of channels (two channels per set)

FIG. 8 is a view showing four almost identical die-cut strips 7 of adhesive tape where each strip 7 of tape engages two slots 8 in the eye shield or guard 26 in accordance with the invention. This view is the concave side 28 which will be in contact with or face the patient's face around the eyes. The adhesion side of the adhesive tape strips 7 facing the patient is ideally wider than the distance between the two slots 8 and higher than the outside edge of the guard 26. When wider (ideally at least 0.25 inches), it is possible that the adhesive tape strips 7 start adhering by making contact to the outside (convex) edge 9. This facilitates a secure beginning adhesion where it becomes possible to weave the adhesive tape strips 7 inside one channel and then outside the second channel. Properly done, the adhesion portion is now facing inward ready to affix to the affected eye (see FIGS. 12-15).

The slots 8 can be shallow having a depth ranging from about 0.25 inches to about 0.5 inches and be clearly out of the range of vision of the patient. The height of the die-cut adhesive tape strips can exceed the height of the edge (when seated in the channel), by about 0.5 inches to about 0.75 inches or in a similar range.

FIG. 9 is a paper strip 10 containing a number of individual die-cut adhesive bandage tapes, strips or pieces 11. Each peel off adhesive piece 11 is ideally about 0.5 inches or slightly more than the widths of the two channels that accept the strip of adhesive. The individual strips can be square cornered or rounded corners (which may be easier to remove), or any type of corner known to those in the medicinal bandage art or label fields. Such a paper strip is included in a system in accordance with the invention, along with the eye shield as in any of the embodiments disclosed herein. However, the eye shield can be provided without the strip of adhesive pieces.

The adhesive used is preferably similar to that of bandage adhesion and is ideally easy to remove as in the case of such products as Band Aid™, etc. It should have similar weight of that of the sanitary bandage rolls administered in hospital. This added weight will facilitate spooling through the parallel or tapered channels in the eye shield in accordance with the invention. Tapered channels may be preferably advantageous insofar as they provide a lead-in passageway for quick engagement on the outside and then spool it through both channels and finally adhere it to the opposite of the far outside edge.

Individual pieces may be attached and separated by easy-to-tear off perforated score lines 110. Yet another variation would be to have substantially similar sized individual die-cut strips 111 spaced apart (as seen by separation areas 112) for easy removal (see FIG. 9A).

FIG. 10 shows the manner for adhering the 0.25 inch outside edge of the adhesive tape strip to the eye shield with it being shown spooling through the first channel 12 of the eye shield.

Figure 11:
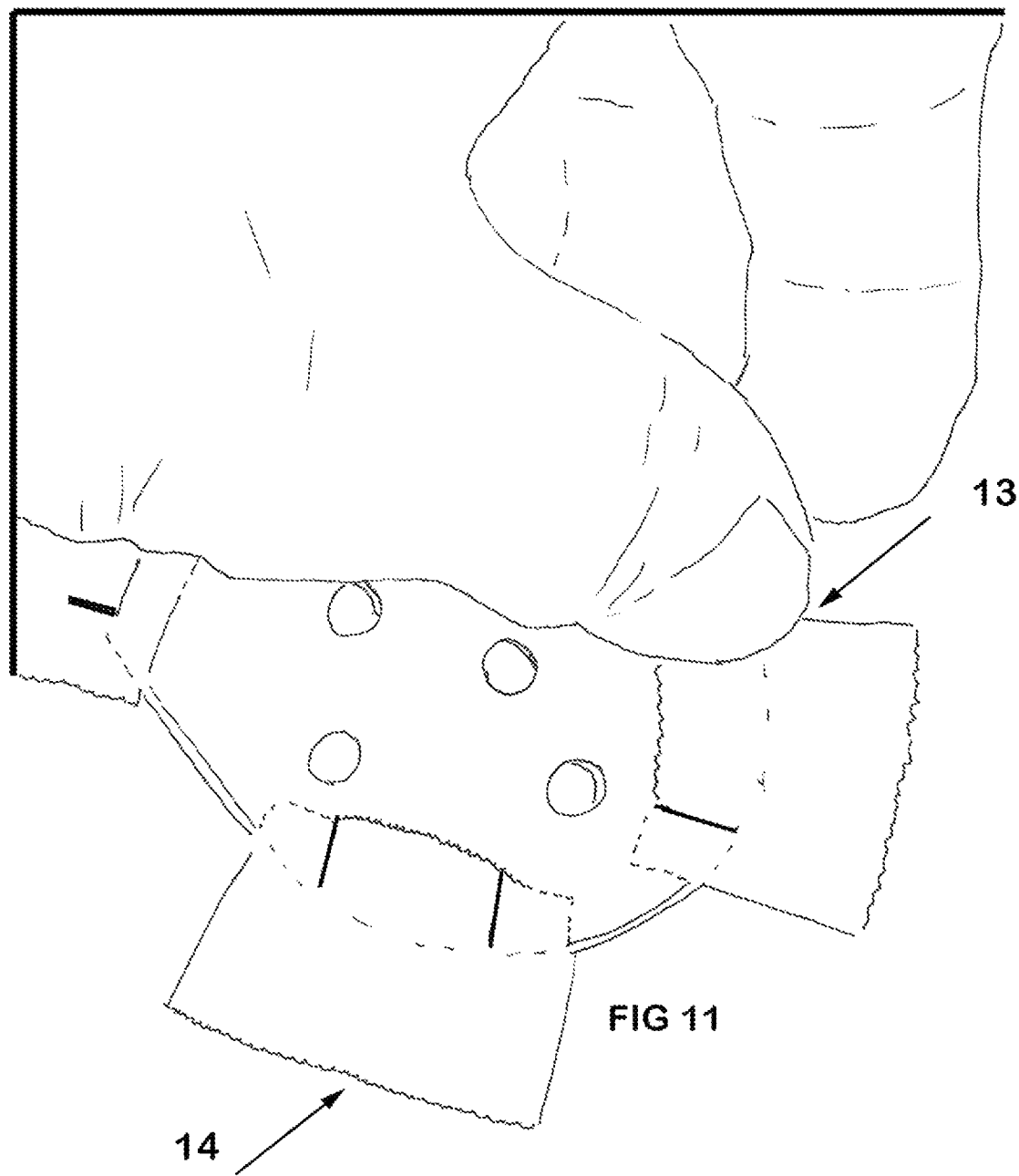
FIG. 11 is a partial frontal view of the eye shield in accordance with the invention facing the direction toward the patient's eye (concave) with one die-cut strip secured to two channels, and one die-cut strip engaged in the first channel and ready to engage the second channel.
Figure 12:
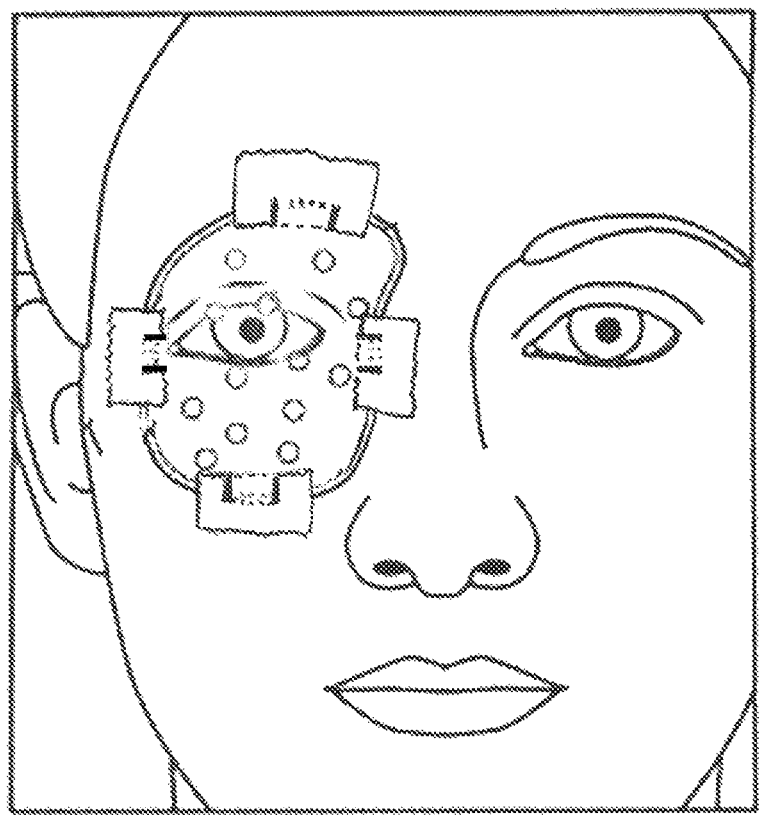
FIG. 12 is a frontal view of the eye shield in accordance with the invention showing the proper positioning of the conventional clear protective right eye shield with four die-cut adhesive strips that engage the eye shield in accordance with the invention and the patient.

FIG. 11 shows the manner for adhering the opposing end of the adhesive tape strips to the outside of the eye shield 13. When use of the eye shield is accomplished as expected and instructed by the personnel or entity provided the eye shield to the patient, each die-cut adhesive tape strip is secured in two places to the outside edge of the eye shield and the majority of adhesive of the adhesive tape strip 14 is facing inward ready to adhere to the patient and in no way interfere with the patient's vision range. In this case, the adhesive tape strip passes through both notches and is alongside the concave side between the notches and over the convex side laterally outside of the notches. A majority of the adhesion portion is thus facing inward, but satisfaction of this condition depends on, for example, the size of the notches, the size of the eye shield, and the adhesive tape strip.

It is possible that less than a majority of the adhesion portion faces inward. It is also possible to apply the adhesive tape strip to pass through both notches while alongside the convex side between the notches and over the concave side laterally outside of the notches. Application of the adhesive tape strips is not critical to the structure of the eye shield, only its use. One skilled in the art would be able to determine the best configuration of adhesive tape strips, vis-à-vis their size and manner of application, to ensure adhesion of the eye shield to the persons' face over their eye. Different people may require different manners of application and possibly different sizes or shapes of adhesive tape portions.

Figure 13:
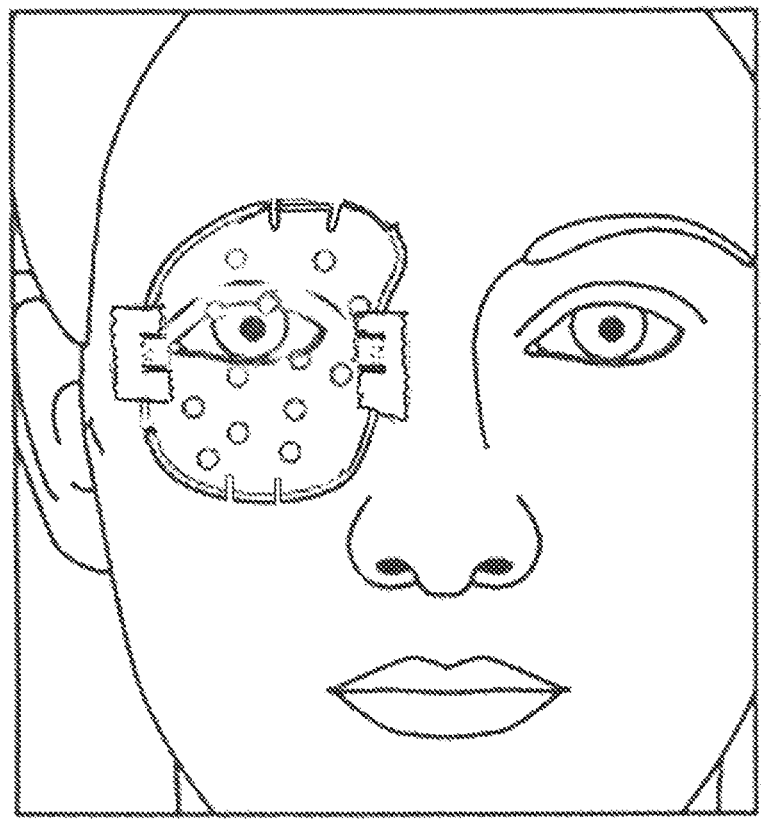
FIG. 13 is a frontal view of the eye shield in accordance with the invention showing the proper positioning of the conventional clear protective right eye shield with two die-cut adhesive strips that engage the eye shield in accordance with the invention and the patient.
Figure 14:
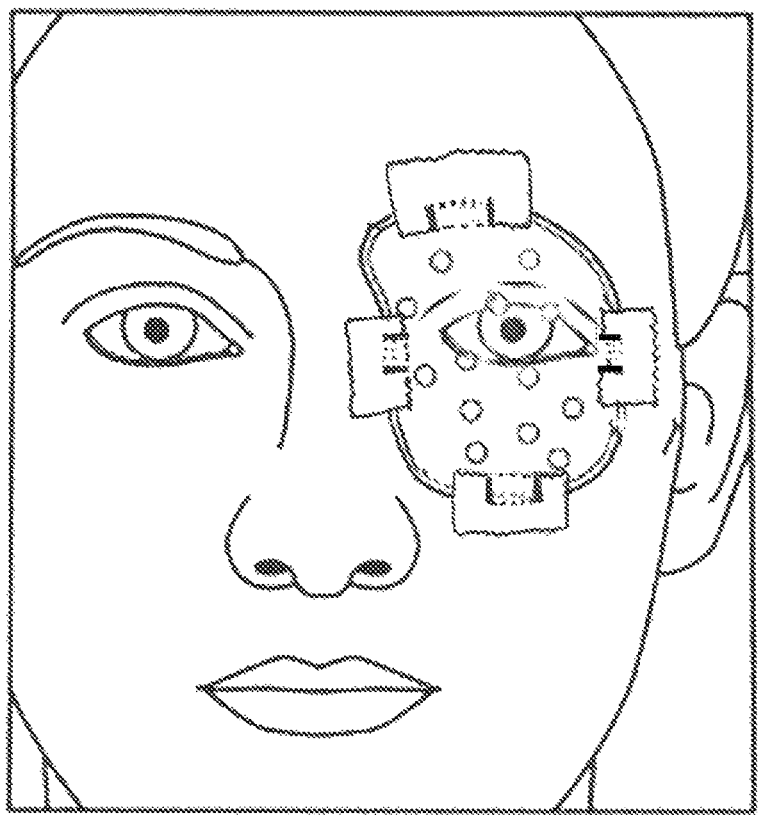
FIG. 14 is a frontal view of the eye shield in accordance with the invention showing the proper positioning of the conventional clear protective left eye shield with four die-cut adhesive strips that engage the eye shield in accordance with the invention and the patient.
Figure 15:
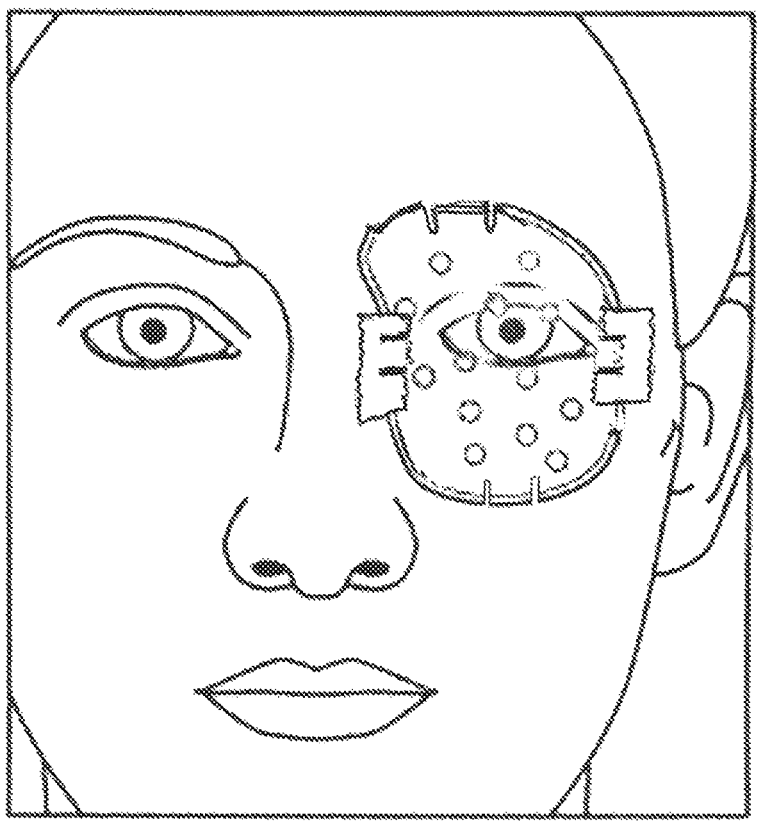
FIG. 15 is a frontal view of the eye shield in accordance with the invention showing the proper positioning of the conventional clear protective left eye shield with two die-cut adhesive strips that engage the eye shield in accordance with the invention and the patient.

FIGS. 12-15 illustrate left and right shields of the eye shield adhered with four guided die-cut adhesive strips (FIGS. 12 and 14) as well as two opposing guided die-cut adhesive strips (FIGS. 13 and 15). In all illustrations, the patient is not visually impeded by randomly placed, often longer than needed strips of adhesive tape (as for a typical use of conventional eye shields). Controlled lengths of identical adhesive tape strips can provide secure engagement of the eye shield in accordance with the invention with minimal skin contact and skin irritation.

At a minimum, in a preferred embodiment, the adhesive strips are placed on opposite sides of the eye shield (i.e., engaged with pairs of notches on opposite sides of the eye shield), and at a maximum, the adhesive strips are placed through every pair of notches on the eye shield.

Another embodiment of an eye shield in accordance with the invention that has the same or similar properties as the eye shield disclosed above is shown in FIG. 16-23. This eye shield has a body that is overmolded and includes resilient, flexible edges with the central area rigid and optically clear. Features disclosed above for the embodiment of FIGS. 6-15 are present in this embodiment and are not described in detail.

Figure 16:
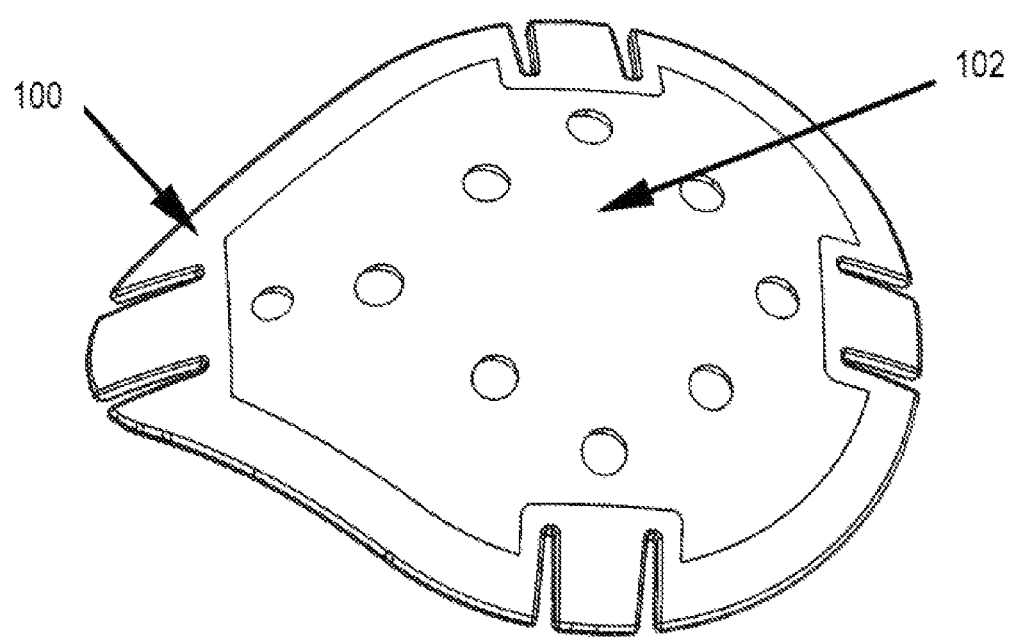
FIG. 16 is a perspective view of another embodiment of an eye shield in accordance with the invention.

FIG. 16 is a perspective view of an eye shield in accordance with the invention having a body that is partly made from soft, overmolded elastomeric material that conforms to a wearer's facial characteristics, at least in a peripheral region 100. The elastomeric material may comprise one or more elastomers. This eye shield is also resilient, preferably about Shore 30A durometer to about Shore 65A, which provides added comfort to the patient over a full circumference. A central area 102 is optically clear and made from acrylic or polycarbonate as disclosed above, or similar material. As such, the central area 102 does not interfere with the wearer's range of vision. Furthermore, peripheral region 100 is sufficiently out of the wearer's range of vision.

The peripheral region 100 preferably surrounds the central region 102, i.e., is interposed between the central region 102 and the edge of the eye shield so that the exposed edge of the eye shield is formed only by the peripheral region 100. Peripheral region 100 also defines the peripheral or circumferential edge of the body of the eye shield.

Figure 17:
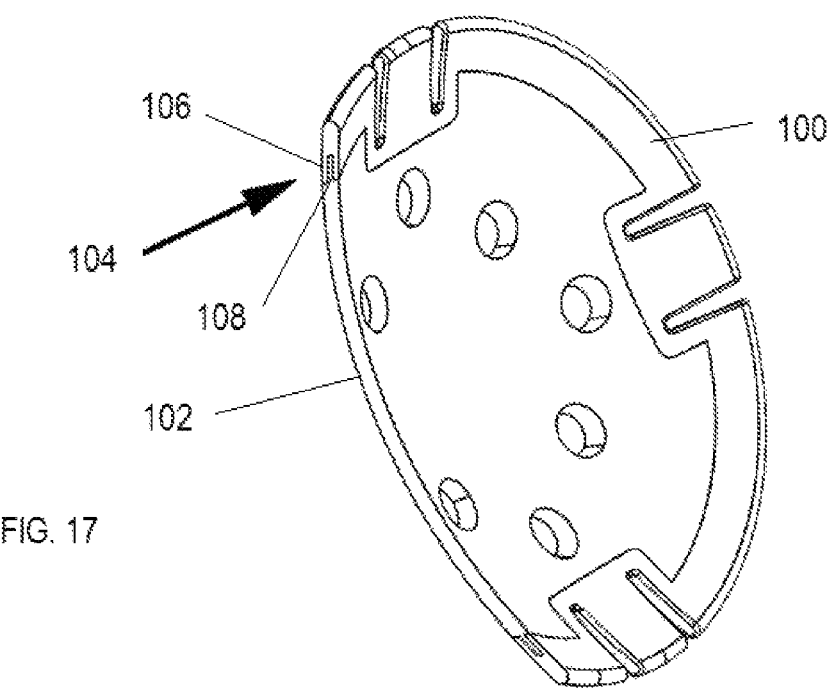
FIG. 17 is a cross-sectional view of the embodiment shown in FIG. 16.
Figure 18:
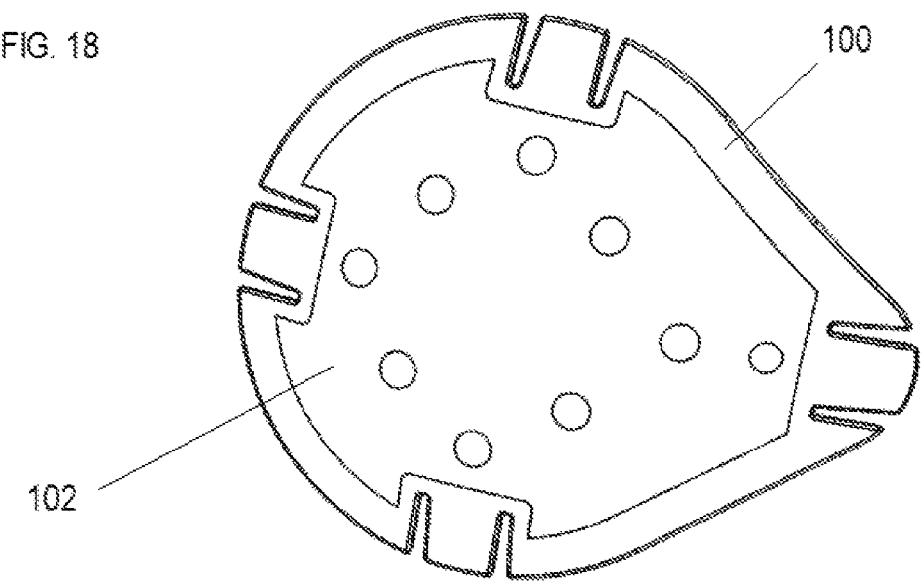
FIGS. 18-23 show additional views of the eye shield shown in FIG. 16.
Figure 19:
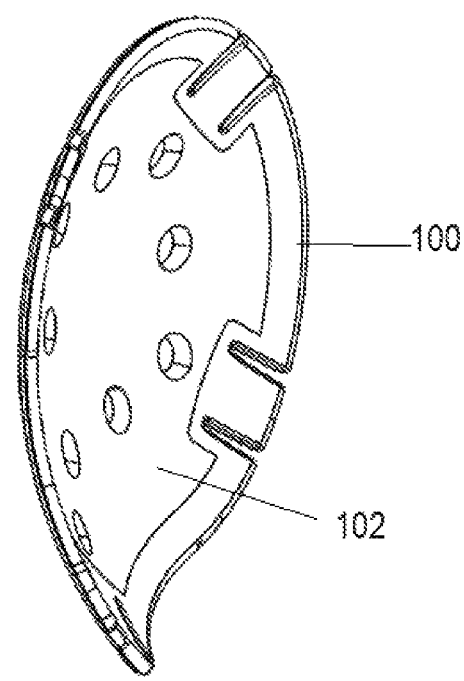
Figure 20:
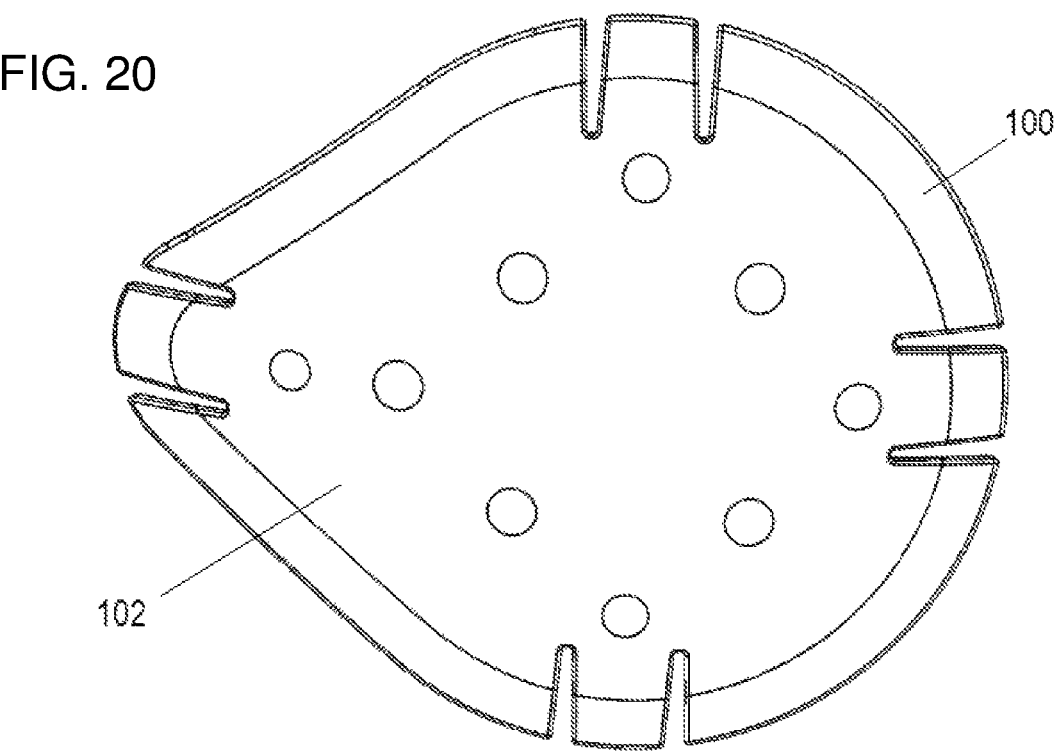
Figure 21:
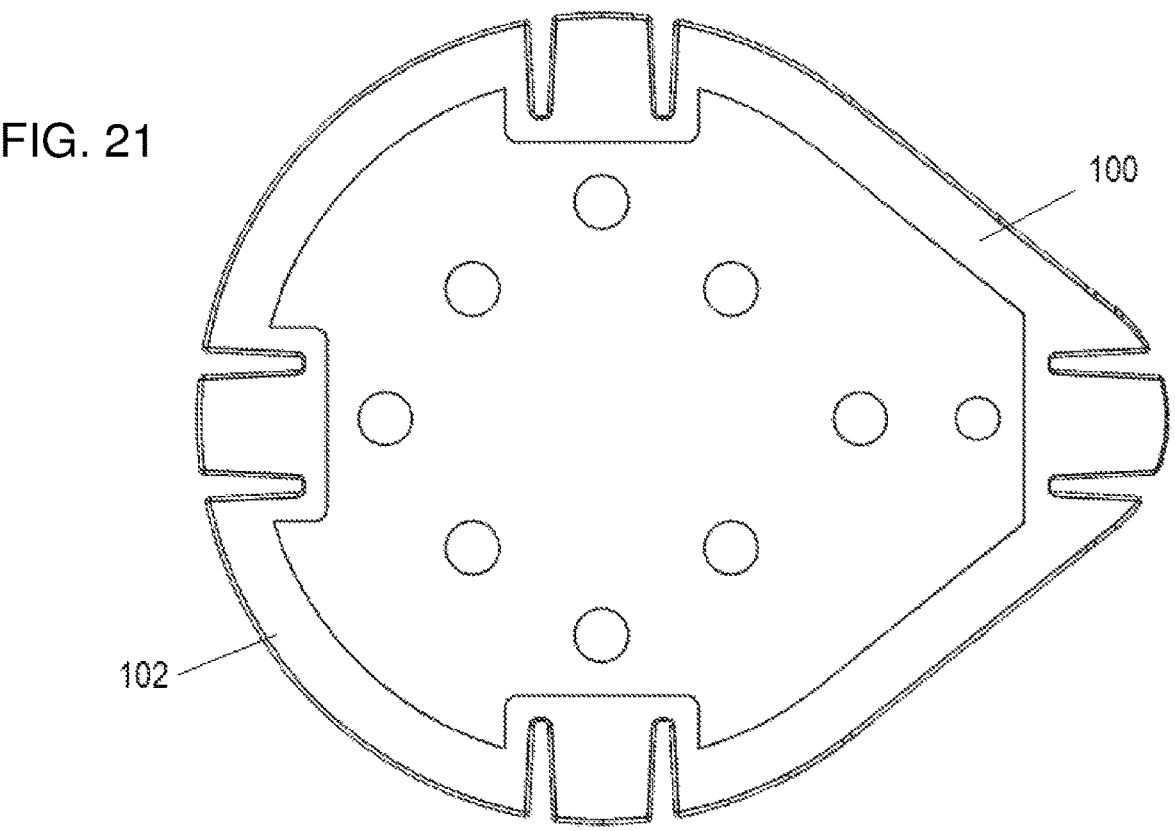
Figure 22:
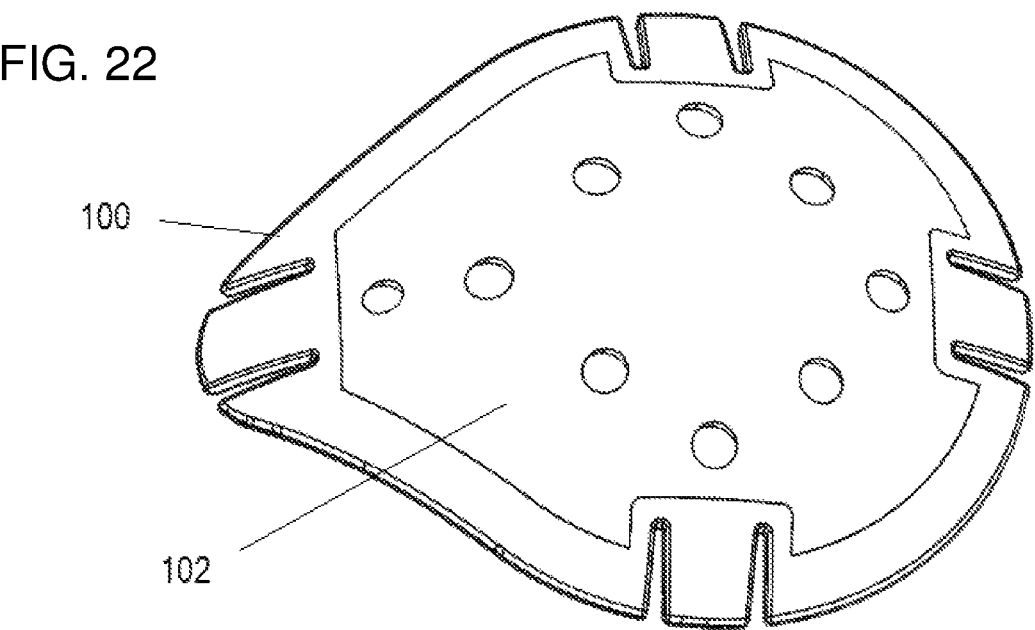
Figure 23:
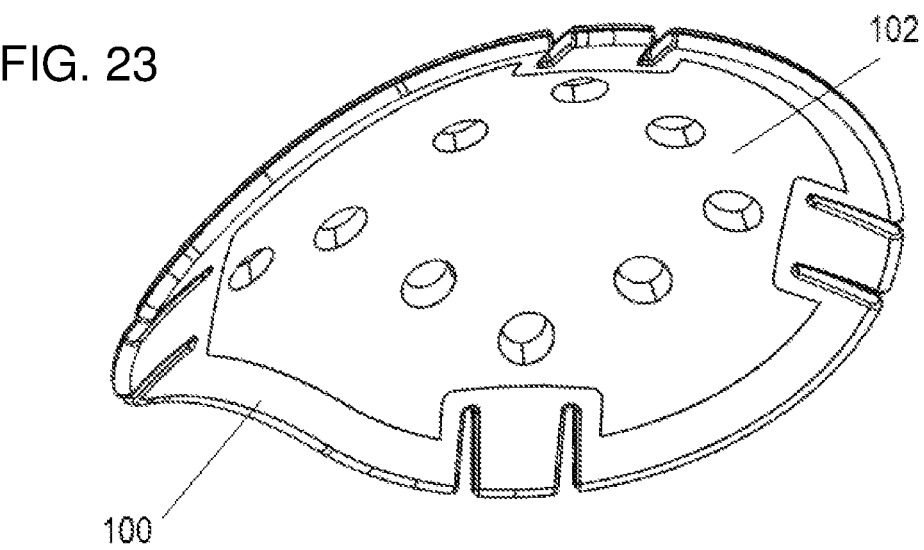

FIG. 17 is a cross-sectional view of the eye shield shown in FIG. 16. As shown, the wall thickness between the two substrates of the peripheral region 100 and the central region 102 is preferably the same. Also visible is the rigid clear part grooved into the soft elastomer edge forming an attachment region 104, e.g., one of the peripheral region 100 and the central region 102 is provided with a tongue 108 and the other with a complementary groove 106. This also provides a more positive adhesion in preventing delamination. As shown, the central region 102 is provided with the tongue 108 and the peripheral region 100 with the groove 106 but the reverse is also envisioned, and should be considered as encompassed within the scope of the invention and claims.

Different attachment means for attaching the central region 102 to the peripheral region 100 are also considered for use in the invention, and would be known to those skilled in the art to which this invention pertains in view of the disclosure herein.

FIGS. 18-23 show additional views of the embodiment of the eye shield shown in FIGS. 16 and 17. Details of the eye shield described above can be seen better in FIGS. 18-23.

Figure 24:
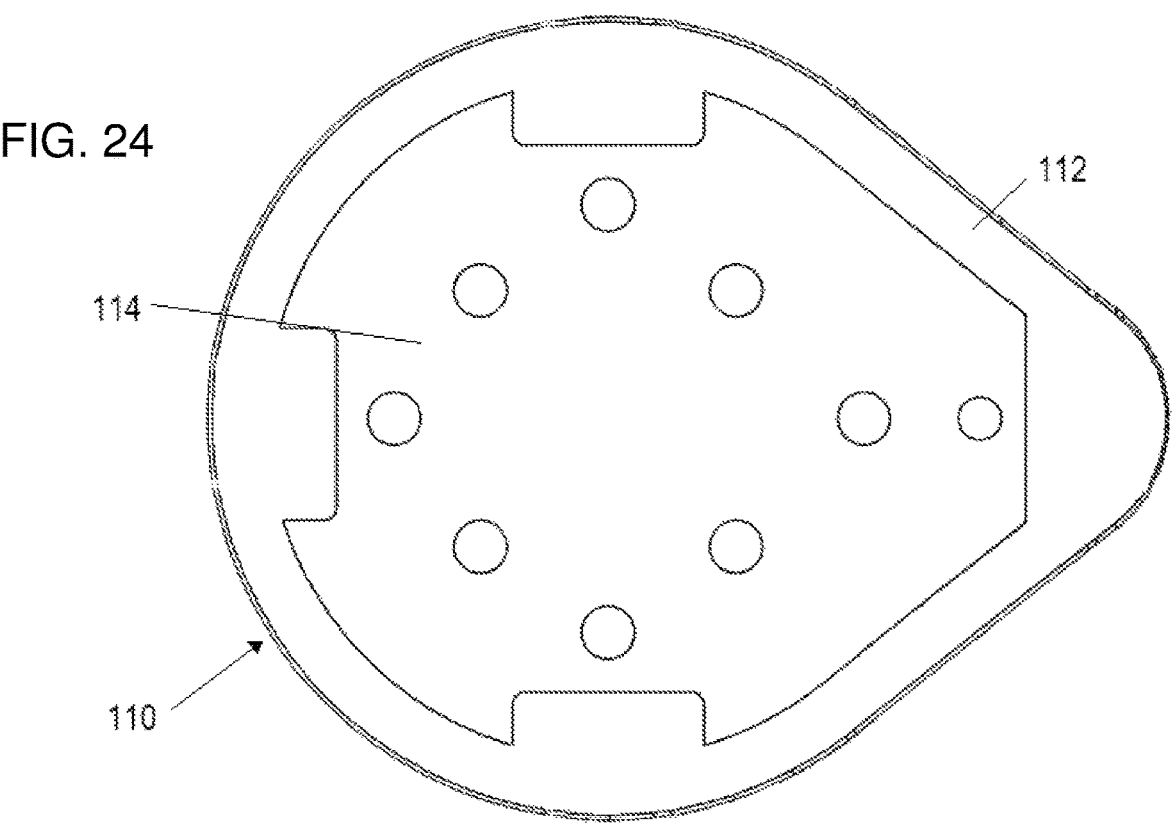
FIG. 24 is a view of an embodiment of an eye shield in accordance with the invention like that shown in FIGS. 16-23 but with uninterrupted circumferential edge on the peripheral region.

FIG. 24 shows an embodiment of an eye shield 110 including a peripheral region 112 and a central region 114 wherein edge of the peripheral region 112 is uninterrupted or continuous, i.e., it does not include channels, openings or slots.

The overmolded embodiments shown in FIGS. 16-24 can be made with the parallel slots, with the tapered slots or with any other type of slots. Ideally, the parallel slotted version is far superior than other slotted versions. A surgeon or other medical personnel can determine which eye shield is best for the patient, and for which situations.

The features of the eye shield disclosed in FIGS. 6-15 may be used in the eye shields disclosed in FIGS. 16-24 and vice versa.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. An eye shield, comprising:
a curved body having a size to cover an eye of a wearer,
said body having a concave side configured to face the eye of the wearer and an opposite convex side,
said body having a circumferential edge and a plurality of openings in a central region surrounded by material of said body,
said body including at least two spaced apart pair of notches on opposite sides of said body, each of said notches of said at least two pair of notches extending inward to a central region of said body from said circumferential edge but not communicating with said openings,
each of said notches defining an opening between opposed surfaces of said body; and
a respective piece of adhesive tape having a length larger than a distance between a respective one of said at least two pair of notches,
whereby said respective piece of adhesive tape is adapted to pass through both of said notches of the respective one of said at least two pair of notches with said respective piece of adhesive tape being alongside said concave side of said body between said notches of the respective one of said at least two pair of notches and over said convex side of said body laterally outside of an area between said notches of the respective one of said at least two pair of notches to thereby enable said body to be secured to the wearer's face over the eye.

2. The eye shield of claim 1, wherein each of said notches of said at least two pair of notches includes a pair of parallel edges to form a parallel opening.

3. The eye shield of claim 1, wherein said body further includes at least one additional spaced apart pair of notches, each of said notches of each of said at least one additional pair of notches extending inward to the central region of said body from said circumferential edge but not communicating with said openings, each of said notches of each of said at least one additional pair of notches defining an opening between opposed surfaces of said body.

4. The eye shield of claim 3, further comprising:
a respective additional piece of adhesive tape having a length larger than a distance between a respective one of said at least one additional pair of notches,
whereby said respective additional piece of adhesive tape is adapted to pass through both of said notches of the respective one of said at least one additional pair of notches with said respective additional piece of adhesive tape being alongside said concave side of said body between said notches of the respective one of said at least one additional pair of notches and over said convex side of said body laterally outside of an area between said notches of the respective one of said at least one additional pair of notches to thereby enable said body to be further secured to the wearer's face over the eye.

5. The eye shield of claim 1, wherein said body has four sides and includes two additional spaced apart pairs of notches, each of said notches of each of said two additional pairs of notches extending inward to the central region of said body from said circumferential edge but not communicating with said openings, each of said notches of each of said two additional pairs of notches defining an opening between opposed surfaces of said body, said at least two pair of notches and said two additional pairs of notches being arranged such that each of said four sides of said body includes a single pair of notches.

6. The eye shield of claim 5, further comprising:
a respective additional piece of adhesive tape having a length larger than a distance between a respective one of said at least two additional pairs of notches,
whereby said respective additional piece of adhesive tape is adapted to pass through both of said notches of the respective one of said at least two additional pairs of notches with said respective additional piece of adhesive tape being alongside said concave side of said body between said notches of the respective one of said at least two additional pairs of notches and over said convex side of said body laterally outside of an area between said notches of the respective one of said at least two additional pairs of notches to thereby enable said body to be further secured to the wearer's face over the eye.

7. The eye shield of claim 1, wherein said central region of said body is optically clear material and a peripheral region surrounding said central region is a resilient flexible material.

8. The eye shield of claim 7, wherein said central region is acrylic or polycarbonate and said peripheral region is elastomeric material.

9. The eye shield of claim 7, further comprising attachment means for attaching said central region to said peripheral region.

10. The eye shield of claim 9, wherein said attachment means comprise cooperating tongue or groove formations.

11. The eye shield of claim 7, wherein said peripheral region includes resilient, flexible edges.

12. The eye shield of claim 11, wherein said peripheral region is material having a hardness of from about Shore 30A to about Shore 65A.

13. The eye shield of claim 1, wherein said body is overmolded and contains two substrates in a unibody construction.

14. A system attachable to a person's face to cover an eye of the person, comprising:
an eye shield including a curved body having a size to cover the eye,
said body having a concave side configured to face the eye and an opposite convex side,
said body having a circumferential edge and a plurality of openings in a central region surrounded by material of said body,
said body including a plurality of spaced apart pairs of notches, each of said notches of said pairs of notches extending inward to a central region of said body from said circumferential edge but not communicating with said openings,
each of said notches defining an opening between opposed surfaces of said body; and a continuous strip of adhesive tape tearable into a plurality of pieces of adhesive tape or a strip comprising a plurality of pieces of adhesive tape at least equal in number to the number of said pairs of notches, each of said pieces of adhesive tape having a length larger than a distance between a respective one of said pairs of notches, whereby said eye shield is configured to be attached to the face of the person to cover the person's eye by passing each of said pieces of adhesive tape through both of said notches of the respective one of said pairs of notches.

15. The system of claim 14, wherein said pieces of adhesive tape are separated on said strip by perforated score lines.

16. The system of claim 14, wherein said pieces of adhesive tape are separated on said strip by separation areas.

17. The system of claim 14, wherein said central region of said body is optically clear material and a peripheral region surrounding said central region is a resilient flexible material.

18. A method for covering an eye of a person, comprising:

positioning an eye shield against a face of the person over the eye, the eye shield comprising a curved body having a size to cover the eye, the body having a concave side configured to face the eye of the wearer and an opposite convex side, the body having a circumferential edge and a plurality of openings in a central region surrounded by material of the body, the body including a plurality of pairs of notches, each of the notches extending inward to a central region of the body from the circumferential edge but not communicating with the openings, each of the notches defining an opening between opposed surfaces of the body; and passing a respective piece of adhesive tape having a length larger than a distance between each of the notches of a respective pair of the notches through both of the notches of the respective pair of notches and against the face of the person to adhere the eye shield to the person's face.

19. The method of claim 18, wherein the step of passing the respective piece of adhesive tape through both of the notches of the respective pair of notches and against the face of the person comprises passing the respective piece of adhesive tape alongside the concave side of the body between the notches of the respective pair of notches and over the convex side of the body laterally outside of an area between the notches of the respective pair of notches.

20. The method of claim 18, further comprising:

forming each piece of adhesive tape from a continuous strip of adhesive tape, or removing each piece of adhesive tape from a strip comprising a plurality of pieces of adhesive tape at least equal in number to the number of the pairs of notches.

* * * * *